(12) United States Patent
Nayak

(10) Patent No.: US 10,888,344 B2
(45) Date of Patent: Jan. 12, 2021

(54) THROMBECTOMY DEVICE

(71) Applicant: Interventional Works, LLC, Grand Rapids, MI (US)

(72) Inventor: Sanjeev Nayak, Staffordshire (GB)

(73) Assignee: Interventional Works, LLC, Grand Rapids, MI (US)

( * ) Notice: Subject to any disclaimer, the term of this patent is extended or adjusted under 35 U.S.C. 154(b) by 144 days.

(21) Appl. No.: 15/769,500

(22) PCT Filed: Oct. 19, 2016

(86) PCT No.: PCT/GB2016/053245
§ 371 (c)(1),
(2) Date: Apr. 19, 2018

(87) PCT Pub. No.: WO2017/068342
PCT Pub. Date: Apr. 27, 2017

(65) Prior Publication Data
US 2018/0303500 A1    Oct. 25, 2018

(30) Foreign Application Priority Data
Oct. 23, 2015    (GB) .................................. 1518780.0

(51) Int. Cl.
*A61B 17/221*    (2006.01)
*A61B 17/3207*    (2006.01)
(Continued)

(52) U.S. Cl.
CPC .... *A61B 17/221* (2013.01); *A61B 17/320725* (2013.01); *A61B 2017/00292* (2013.01); *A61B 2017/22034* (2013.01)

(58) Field of Classification Search
CPC .......... A61F 2002/011; A61F 2002/016; A61F 2002/018; A61F 2230/006; A61F 2230/0067; A61F 2230/0069; A61F 2/01; A61F 2/90; A61F 2230/0017; A61F 2230/0034; A61F 2/013; A61F 2/91; A61F 2/92; A61F 2/95; A61F 2/915; A61F 2/89;
(Continued)

(56) References Cited

U.S. PATENT DOCUMENTS

| 5,800,525 A * | 9/1998 | Bachinski | A61F 2/01 606/200 |
| 2003/0069596 A1* | 4/2003 | Eskuri | A61F 2/013 606/200 |
| 2012/0083868 A1* | 4/2012 | Shrivastava | A61F 2/95 623/1.11 |

FOREIGN PATENT DOCUMENTS

| DE | 102011101522 A1 | 11/2012 |
| WO | 03077799 A2 | 9/2003 |
| WO | 2012120490 A2 | 9/2012 |

OTHER PUBLICATIONS

International Search Report and Written Opinion for corresponding International Application No. PCT/GB2016053245, dated Nov. 22, 2016.

* cited by examiner

*Primary Examiner* — Mohamed G Gabr
(74) *Attorney, Agent, or Firm* — McGarry Bair PC

(57) ABSTRACT

A thrombectomy device including a profiled member made from a piece of mesh material. The piece in a relaxed condition in axial cross section has a generally cylindrical outer profile. The piece includes a central cross part with a generally S shaped profile, with respective side parts extending circumferentially in a clockwise direction from each end of the cross part, to provide a free end located adjacent an opposite end of the cross part.

19 Claims, 8 Drawing Sheets

(51) Int. Cl.
*A61B 17/22* (2006.01)
*A61B 17/00* (2006.01)

(58) Field of Classification Search
CPC .... A61F 2/86; A61F 2/93; A61F 2/844; A61F 2/852; A61F 2/954; A61B 17/221; A61B 17/320725; A61B 17/12118; A61B 17/12022; A61B 17/22; A61B 17/12145; A61B 2017/00778; A61B 17/12031; A61B 17/12109; A61B 17/12113; A61B 17/12168; A61B 17/12172; A61B 17/1204; A61B 2017/00292; A61B 2017/22034; A61B 2017/2215; A61B 2017/2212; A61B 2017/00867; A61B 2017/22094
See application file for complete search history.

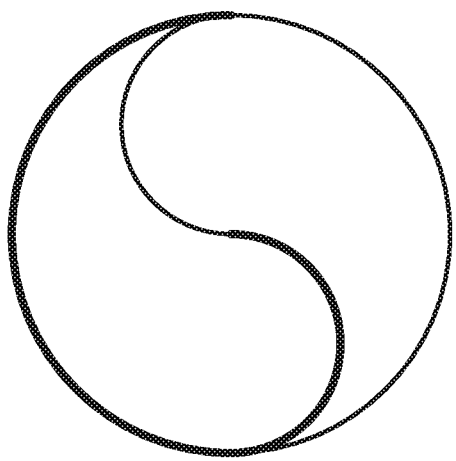
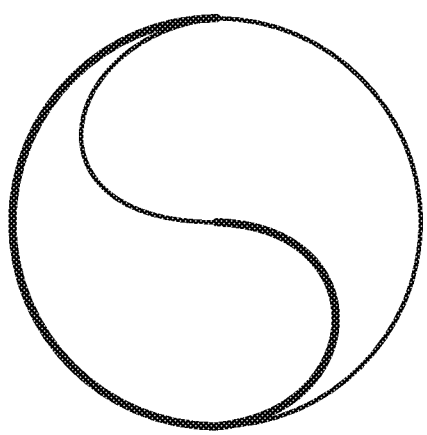
FIG. 2D          FIG. 2C
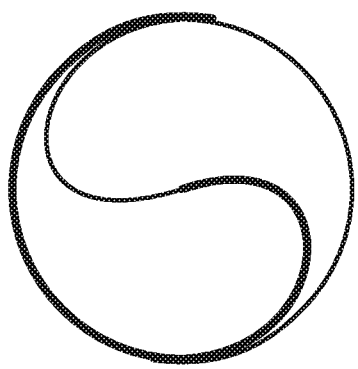
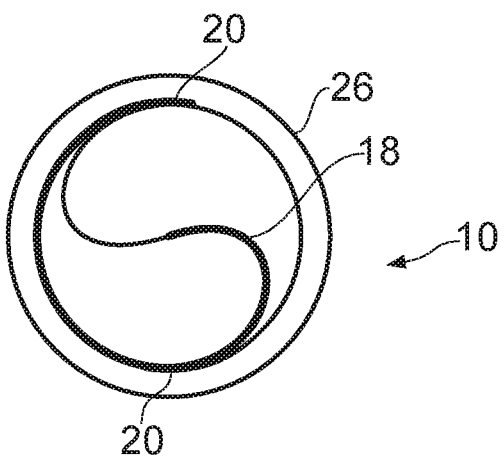
FIG. 2B          FIG. 2A

THROMBECTOMY DEVICE

RELATED APPLICATIONS

The present invention is a U.S. National Stage under 35 USC 371 patent application, claiming priority to Serial No. PCT/GB2016/053245, filed on 19 Oct. 2016; which claims priority of GB 1518780.0, filed on 23 Oct. 2015, the entirety of both of which are incorporated herein by reference.

This invention relates to a thrombectomy device, and particularly but not exclusively a thrombectomy device for removing thrombi from the cerebral vasculature of patients.

Thromboembolic diseases such as large vessel cerebral occlusion (stroke), myocardial infarction, pulmonary embolism and peripheral thrombosis are typically triggered by a thrombus. Thrombus is a blood clot composed of blood platelets, fibrinogen, clotting factors, etc., which forms a conglomerate and adheres to blood vessel and occludes it entirely or partly. An occlusion of organ arteries leads to an interruption in the supply of the dependent tissue with oxygen and nutrients. Within a short period of time, this leads to destruction of the affected tissue (infarct). The most common affected vessels are the heart and the brain, but any other body organs and limbs can be affected.

Transluminal and/or endovascular catheter-guided interventional therapy methods are increasingly applied in state-of-the-art technology because these methods are less invasive. There are also other devices available to remove a thrombus by means of suction catheters generating a negative pressure.

Ischemic strokes are caused by a cerebral vessel occlusion usually treated with an intravenous thrombolytic agent. The thrombolytic treatment methods are rarely successful once the available time frame or treatment window has elapsed.

A number of prior thrombectomy devices have been proposed, generally in the form of an open stent or a tubular device made of mesh material. Such devices often have a relatively low tensile force or spring load when moving to a relaxed condition. This can mean that there is not a sufficient shear force on the thrombus sitting in the vessel wall so that residues remain in the vessel. This necessitates numerous applications of such devices into the cerebral blood vessels, increased number of passes, for subsequent thrombi removal.

According to a first aspect of the invention there is provided a thrombectomy device, the device including a profiled member of a mesh material, the profiled member having an axial cross-section in a relaxed condition which provides a generally circular outer profile to define a circle, a profiled cross part extending across the circle, with respective side parts extending from respective ends of the cross part circumferentially around the circle to provide free ends substantially adjacent the opposite ends of the cross part, which profiled member can be moved to a smaller axial cross-section and retained thereat, to permit location at a required position.

The profiled member may have a generally cylindrical outer profile in a relaxed condition.

In one arrangement the profiled cross part may have a generally S shape in axial cross-section.

In a further arrangement the cross part may comprise three interconnected members extending outwardly from the axis, with respective side parts extending from each end of a one of the interconnected members.

The respective side parts may extend in a clockwise direction from the ends of the cross part.

The profiled member may be configured such that as the profiled member is moved to a smaller axial cross-section, the side parts overlap each other, so as to reduce the outer profile circumference of the profiled member.

The profiled member may be formed from a rectangular piece of mesh material. A tab may extend from one side of the rectangle to provide a mounting location for a guide wire. The tab may have a V shape, with the V pointing away from the rectangle.

The tab may be located so as to extend from the cross part of the profiled member, and may extend substantially from the centre of the cross part.

The tab may be provided towards one side of the rectangular piece of mesh material.

The device may include a guide wire to enable the profiled member to be moved to and from a required location.

The guide wire may extend substantially from the centre of the cross part.

The guide wire may be mounted to the tab.

The guide wire may extend across the profiled member, and may extend across the whole length of the profiled member.

The device may include a sleeve locatable initially on the profiled member so as to retain the profiled member in a condition with a smaller axial cross-section than in a relaxed condition, the sleeve being removable from the profiled member when in a required position, to permit the profiled member to move to or towards a relaxed condition.

The profiled member may be made of a braided mesh material, or a cut mesh material.

The mesh material may have a shape memory. The mesh material may be metal and may be an iron alloy such as stainless steel or spring steel.

The mesh material may be any of cobalt-chromium alloys, binary nickel titanium alloys, or ternary nickel titanium-chromium alloys.

Embodiments of the present invention will now be described by way of example only and with reference to the accompanying drawings, in which:—

FIGS. 2A to 2D are sequential cross-sectional end views of part of the first device moving between a stored condition to the use condition;

Figure 1:
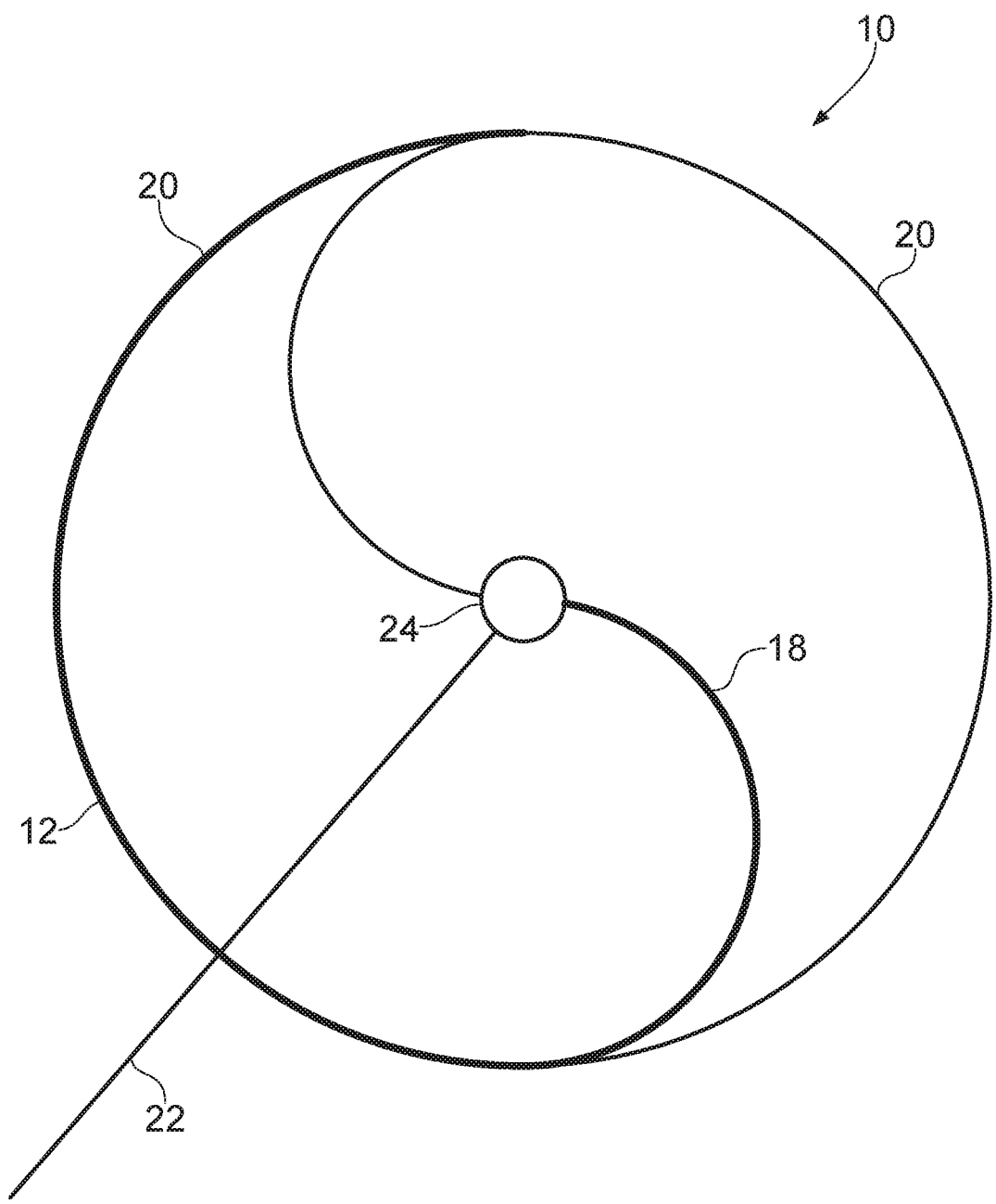
FIG. 1 is a diagrammatic cross-sectional end view of a part of a first thrombectomy device in a use condition.
Figure 3:
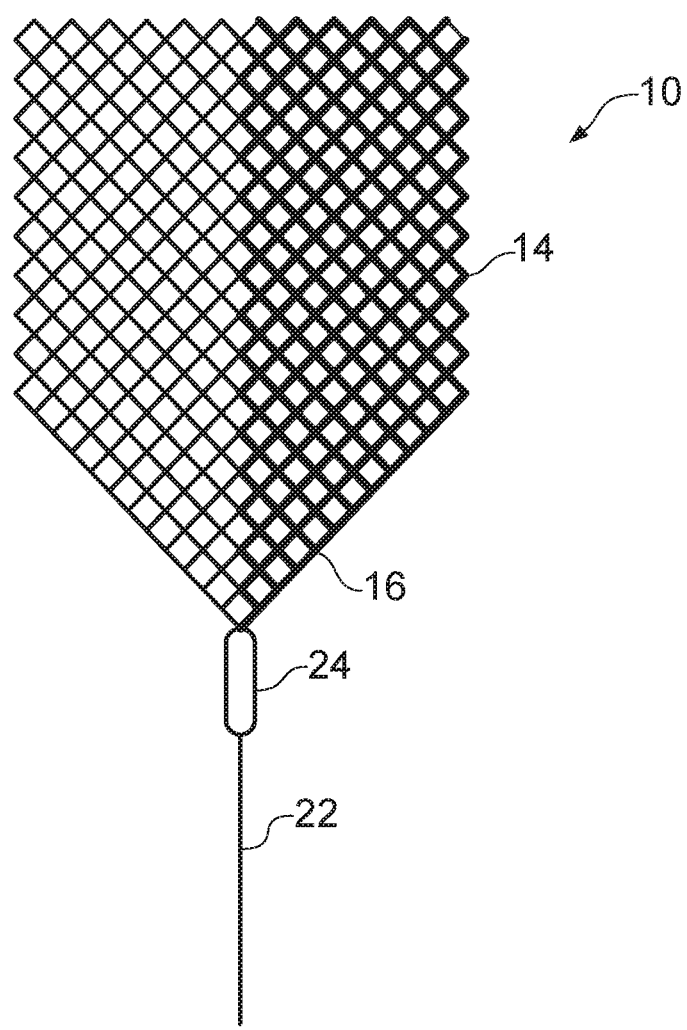
FIG. 3 is a diagrammatic plan view of part of the first device in a further condition.

FIGS. 1 to 3 of the drawings show a first thrombectomy device 10 suitable as hereinafter will be described for removing thrombi from the thrombotic cerebral vessel. The device 10 includes a profiled member 12. The member 12 is made from a piece 14 of mesh material as shown in FIG. 3. Any appropriate mesh may be used, which may be open cell, or closed cell or a mixture of the two, at different parts of the profiled member 12. Different mesh sizes may be chosen as appropriate such as for example 2 mm, 2.5 mm, 2.75 mm, 3 mm.

The piece 14 is generally rectangular with a V shaped tab 16 extending from one side, the proximal side in use, of the rectangle. The tab 16 extends across the whole of the proximal side of the piece 14. The mesh in this instance is made from a shape memory binary nickel titanium alloy, Nitinol.

The piece 14 of mesh is formed by heat treatment or otherwise, to the shape shown in FIG. 1 in a relaxed condition, which in axial cross-section has a generally cylindrical outer profile. The cylinder has a central cross part 18 which has a generally S shaped profile. Respective side parts 20 extend circumferentially in a clockwise direction from each end of the cross part 18, to provide a free end located adjacent the opposite end of the cross part 18.

The profiled member 12 is formed such that in a relaxed condition it will return to the profile shown in FIG. 1. The device 10 also includes a guide wire 22 which has a coupling element 24 at one end which is mountable to the apex of the tab 16 as shown in FIG. 3.

To locate the device 10 in the thrombotic cerebral vessel of a patient, it is first compressed to the form shown in FIG. 2A and located in a sheath 26 to retain the profiled member in the condition shown in FIG. 2. As can be seen in moving the profiled member 12 to the condition in FIG. 2, the free ends of the side parts 20 each rotate in a clockwise direction and respectively overlap each other. The device 10 is now ready for use.

In use the device 10 is moved by means of a catheter to the point of application in the thrombotic cerebral vessel, at the location of a thrombus. The guide wire 22 and/or profiled member 12 may be provided with markers in a usual manner which are radiopaque, such that they can be visualised under fluoroscopy.

Once in the required location, the sheath 26 is removed and the profiled member 12 expands to or towards the use condition shown in FIGS. 1 and 2D, through the conditions shown in FIGS. 2B and 2C. As the profiled member 12 expands it opens out, with the side parts 20 moving in an anti-clockwise direction to or towards the condition shown in FIGS. 1 and 2D. The profiled member 12 adapts itself to the vessel lumen. The overlapping of the side parts 20, and also the S shaped cross part 18 provide a greater surface area than previous proposals, to engage with the thrombus. Once the thrombus material is caught in the mesh of the profiled member 12, the device 10 is retracted into the guide catheter.

Parts of the thrombus adhering to the mesh are entrained by the shear effect of the meshes in their overlapping mechanism, and the free edges of the side parts. The profile of the cross part provides a greater radial force to the device relative to previous arrangements and assists in clot capture in conjunction with the overlapping mechanism of the site parts.

The provision of the V shaped tab helps to reduce the potential for the device from reducing in diameter as it is pulled into the catheter. The device provides a large contact area for engagement with a thrombus, and with a strong radial force to the profile, particularly of the S shaped cross part.

Figure 4:
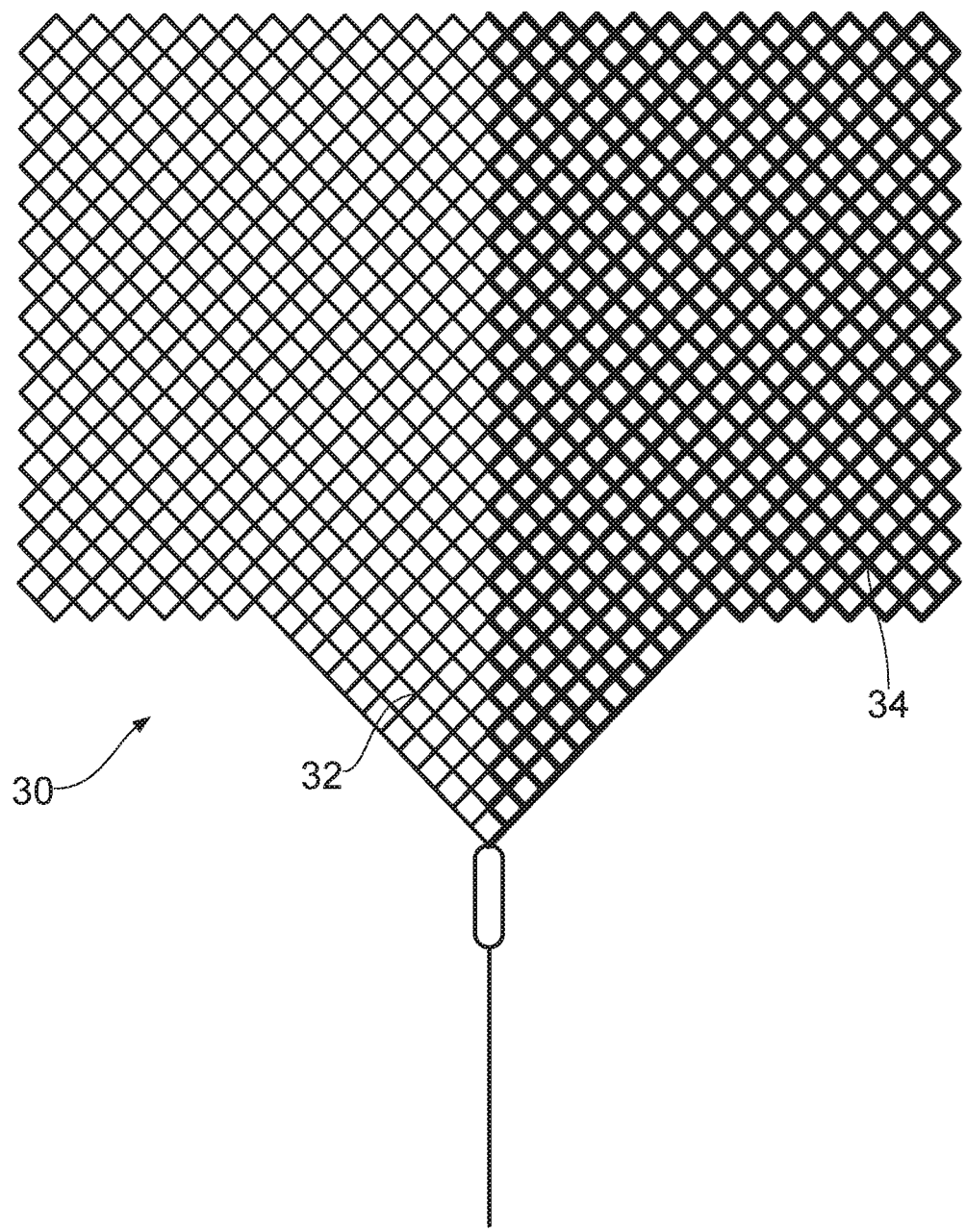
FIGS. 4, 5 and 6 are similar views to FIG. 3 but of respectively second, third and fourth thrombectomy devices.

FIG. 4 shows a second thrombectomy device 30 prior to heat treatment. In this instance a tab 32 only extends from a central part of the rectangle of the piece 34 of mesh.

Figure 5:
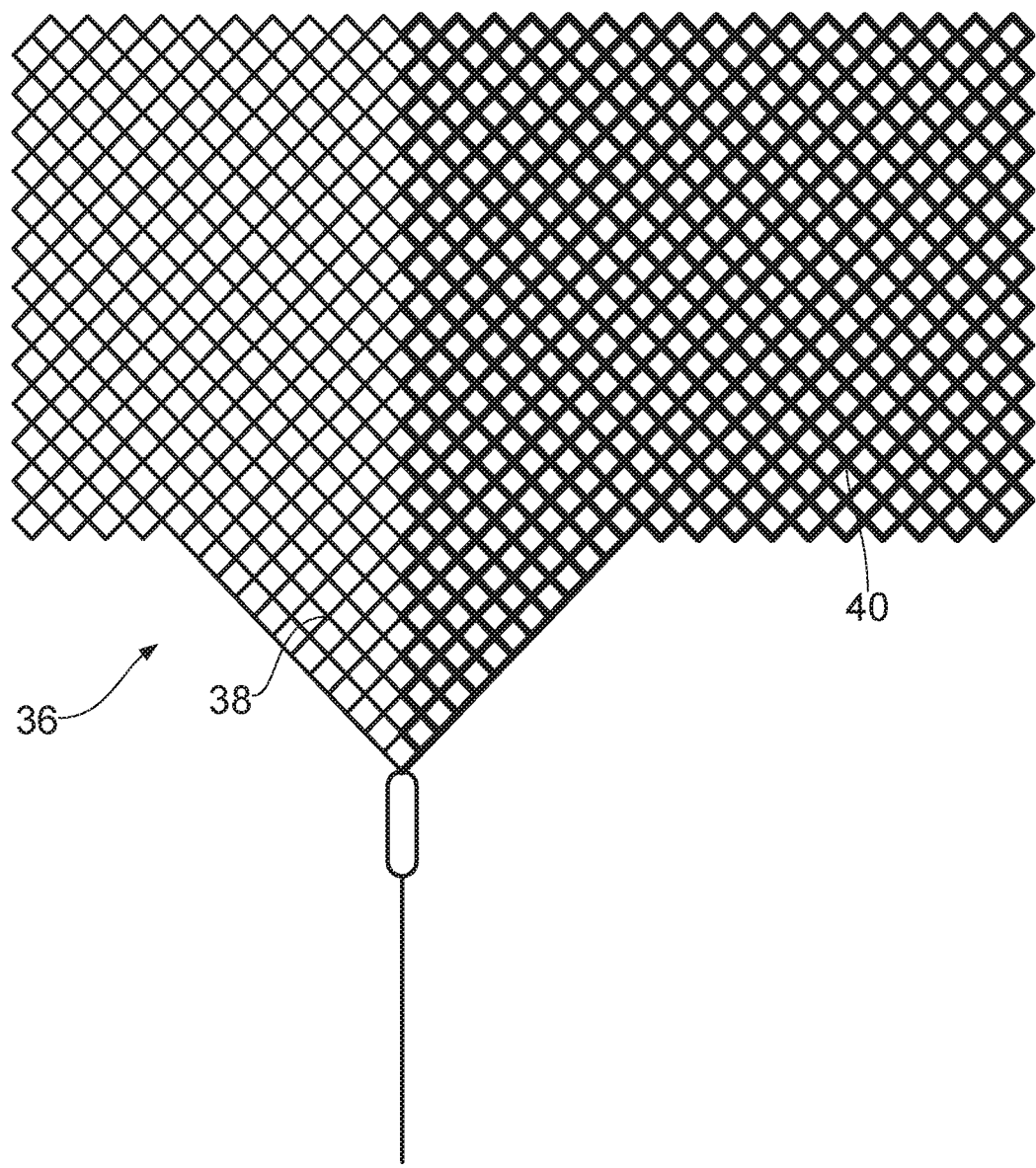

FIG. 5 shows a similar view to FIG. 4 of a third thrombectomy device 36. In this instance the tab 38 only extends for part of the side of the piece 40 of mesh, and the tab is offset from the centre of the piece 40.

Figure 6:
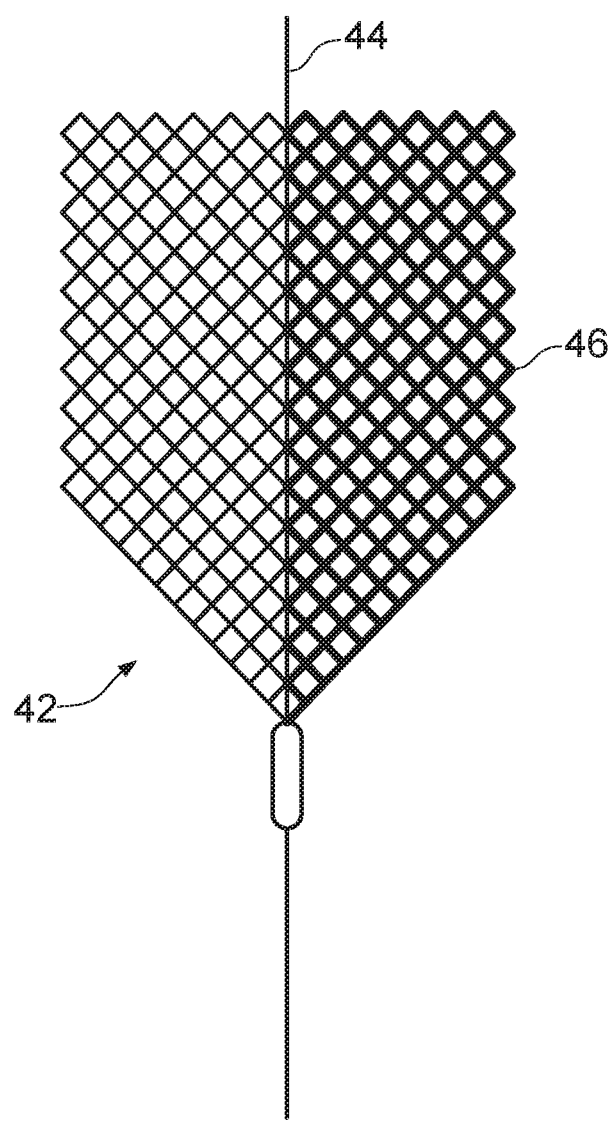

FIG. 6 shows a fourth thrombectomy device 42 which is similar to the device 10 except in this instance a guide wire 44 extends across the whole width of the piece 46 of mesh and beyond. In use this can provide additional stability for the profiled member formed from the piece 46 of mesh.

Figure 7:
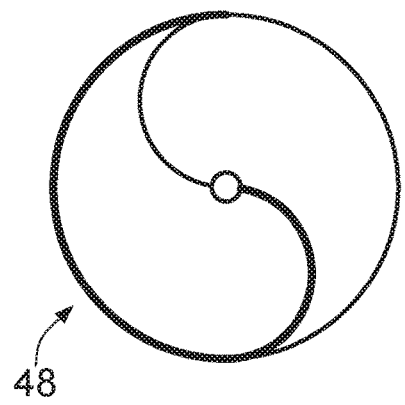
FIG. 7 is a similar view to FIG. 1 but of a fifth thrombectomy device.
Figure 8:
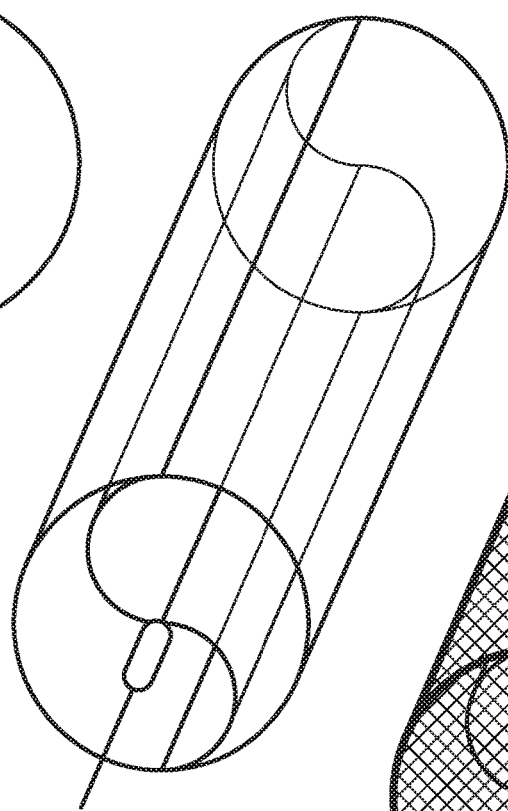
FIGS. 8 and 9 are diagrammatic perspective views of the device of FIG. 7.
Figure 9:
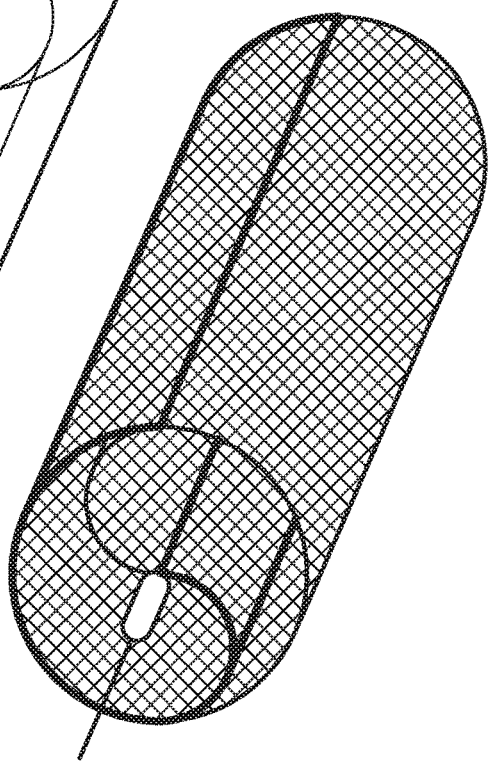

FIGS. 7 to 9 show a fifth thrombectomy device 48. The device 48 is similar to the device 10 except that no tab is provided. FIG. 8 shows the device in a use condition but with most of the mesh not shown in detail to help clarify the profile of the device 48. The full mesh is shown in FIG. 9.

Figure 10:
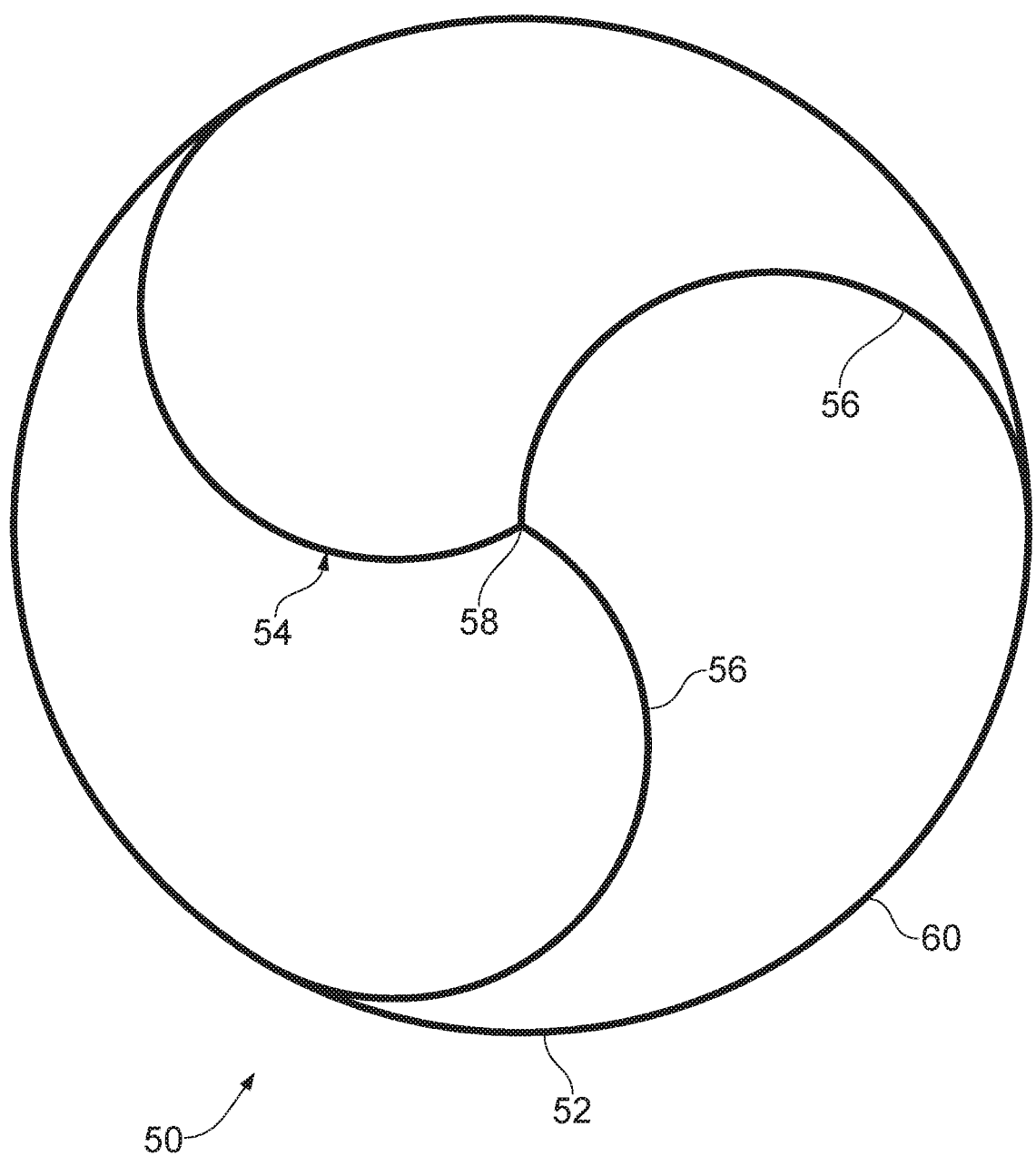
FIG. 10 is a similar view to FIG. 1 but of a sixth thrombectomy device.

FIG. 10 shows a fifth thrombectomy device 50 which in this instance has a profiled member 52 with a cross part 54 which comprises three curved members 56 extending from the central axis 58, and each connected to one of three respective arcuate side parts 60.

There are thus described thrombectomy devices which provide a number of advantageous features providing for improved performance in greater thrombus capture relative to prior arrangements, and thereby reducing the number of required applications of the device. The devices can however readily be manufactured using conventional techniques and operated in a conventional manner. The devices can be provided in required sizes for respective arteries, and could for example be provided in 4.5, 5.5 and 6.5 mm diameters, and at required lengths.

Various other modifications may be made without departing from the scope of the invention. For instance whilst a cut mesh usually cut by laser has generally been found to be preferable, it may be that a braided mesh could be used. A range of different materials could be used for the mesh such as iron alloys including stainless steel or spring steel. Other alloys such as cobalt-chromium alloys or ternary nickel titanium-chromium alloys could also be used. It may for instance be possible for non-metallic materials to be used if they are able to provided the required physical characteristics. The guide wire may be mounted to the profiled member in a different way.

Whilst in a number of the devices an S shape cross part has been described, the cross part could be in the form of a reversed S with the side parts extending in an anti-clockwise direction therefrom. The cross piece may take other shapes. The fifth embodiment has three parts to the cross piece, and it may be possible for the cross piece to include differing numbers of elements. It is to be realised that any combination of the above features may be provided.

Whilst endeavouring in the foregoing specification to draw attention to those features of the invention believed to be of particular importance it should be understood that the Applicant claims protection in respect of any patentable feature or combination of features hereinbefore referred to and/or shown in the drawings whether or not particular emphasis has been placed thereon.

The invention claimed is:

1. A thrombectomy device comprising a profiled member of at least two members of mesh material extending from a central axis and forming a cross part in axial cross-section, each of the at least two members of mesh material having a respective side parts extending annularly about the central axis from the cross part to a free end substantially adjacent an opposite end of the cross part, wherein the profiled member in cross section has a generally cylindrical outer profile in a relaxed condition that can be moved to a smaller axial cross-section and retained thereat, to permit location at a required position in a thrombotic vessel.

2. The thrombectomy device according to claim 1, in which the cross part has a generally S shape in axial cross-section.

3. The thrombectomy device according to claim 1, in which the cross part comprises three members of mesh material extending from the central axis.

4. The thrombectomy device according to claim 1, in which the respective side parts extend in a clockwise direction from the cross part.

5. The thrombectomy device according to claim 1, in which the profiled member is configured such that as the profiled member is moved to a smaller axial cross-section, the side parts overlap each other, so as to reduce the circumference of the outer profile of the profiled member.

6. The thrombectomy device according to claim 1, in which the profiled member is formed from a single rectangular piece of mesh material, a portion of which forms each of the at least two members of mesh material.

7. The thrombectomy device according to claim 6, in which a tab extends from one side of the single rectangular piece of mesh material to provide a mounting location for a guide wire.

8. The thrombectomy device according to claim 7, in which the tab has a V shape, with the V pointing away from the single rectangular piece of mesh material.

9. The thrombectomy device according to claim 7, in which the tab is located so as to extend from the cross part of the profiled member.

10. The thrombectomy device according to claim 9, in which the tab extends substantially from the centre of the cross part.

11. The thrombectomy device according to claim 9, in which the tab is provided towards one side of the rectangular piece of mesh material.

12. The thrombectomy device according to claim 1, in which the thrombectomy device includes a guide wire to enable the profiled member to be moved to and from a required location.

13. The thrombectomy device according to claim 12, in which the guide wire extends across the profiled member along the central axis.

14. The thrombectomy device according to claim 1, in which the thrombectomy device includes a sleeve locatable initially on the profiled member so as to retain the profiled member in a condition with a smaller axial cross-section than in a relaxed condition, the sleeve being removable from the profiled member when in a required position, to permit the profiled member to move to or towards the relaxed condition.

15. The thrombectomy device according to claim 1, in which the profiled member is made of a braided mesh material.

16. The thrombectomy device according to claim 1, in which the profiled member is made of a cut mesh material.

17. The thrombectomy device according to claim 1, in which the mesh material has a shape memory.

18. The thrombectomy device according to claim 1, in which the mesh material is metal.

19. The thrombectomy device according to claim 18, in which the mesh material is any of an iron alloy, stainless steel or spring steel, cobalt-chromium alloys, binary nickel titanium alloys, or ternary nickel titanium-chromium alloys.

* * * * *

UNITED STATES PATENT AND TRADEMARK OFFICE
CERTIFICATE OF CORRECTION

| | |
|---|---|
| PATENT NO. | : 10,888,344 B2 |
| APPLICATION NO. | : 15/769500 |
| DATED | : January 12, 2021 |
| INVENTOR(S) | : Nayak |

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 136 days.

Signed and Sealed this
Fourteenth Day of February, 2023

Katherine Kelly Vidal
*Director of the United States Patent and Trademark Office*